(12) United States Patent
Sarkadi et al.

(10) Patent No.: US 6,297,216 B1
(45) Date of Patent: Oct. 2, 2001

(54) COMPOUNDS FOR REVERSING DRUG RESISTANCE

(75) Inventors: Balazs Sarkadi; Janos Seprodi; Orsolya Csuka; Maria Magocsi; Imre Mezo; Istvan Palyi; Istvan Teplan; Zsolt Vadasz; Borbala Vincze, all of Budapest (HU)

(73) Assignee: Solvo Biotechnology, Szeged (HU)

(*) Notice: Subject to any disclaimer, the term of this patent is extended or adjusted under 35 U.S.C. 154(b) by 0 days.

(21) Appl. No.: 08/737,255

(22) PCT Filed: May 12, 1995

(86) PCT No.: PCT/IB94/00144

§ 371 Date: Feb. 19, 1997

§ 102(e) Date: Feb. 19, 1997

(87) PCT Pub. No.: WO95/31474

PCT Pub. Date: Nov. 23, 1995

(51) Int. Cl.[7] .......................... A61K 38/04; A61K 38/05; C07K 5/06

(52) U.S. Cl. .................. 514/17; 514/18; 514/19; 530/330; 530/331

(58) Field of Search ................. 514/17, 18, 19; 530/330, 331

(56) References Cited

U.S. PATENT DOCUMENTS

| | | | |
|---|---|---|---|
| 3,862,925 | * 1/1975 | Sarantakis et al. | 260/112.5 |
| 3,882,098 | * 5/1975 | Sarantakis | 260/112.5 |
| 4,028,319 | 6/1977 | Jones, Jr. et al. | 260/112.5 |
| 4,277,393 | * 7/1981 | Sakakibara et al. | 260/112.5 |
| 4,318,847 | * 3/1982 | Umezawa et al. | 260/112.5 |
| 4,497,801 | * 2/1985 | Hashimoto et al. | 514/15 |
| 4,637,997 | * 1/1987 | Jolles et al. | 514/17 |
| 4,707,541 | * 11/1987 | Diaz et al. | 530/324 |
| 4,772,587 | * 9/1988 | Tanaka et al. | 514/17 |
| 4,873,342 | * 10/1989 | Tanaka et al. | 514/19 |

FOREIGN PATENT DOCUMENTS

1544778-A    2/1990 (SU) .

OTHER PUBLICATIONS

File Caplus on STN. AN No: 1979:575708. Prusakov et al. 'Synthesis of Gastrin Terminal Fragments and Their Coupling to Proteins', Bioorg. Chim. vol. 4, No. 4, pp. 497–507. Abstract and Strucuter only, 1979.*
Carey, F.A., Organic Chemistry, McGraw–Hill, New York, pp. 1113–1118, 1987.*
Rudinger, J. (1976). Peptide Hormones (ed. J.A. Parsons). University Park Press. Baltimore. pp. 1–7, 1976.*
Dalton et al., "Drug–Resistance in Multiple Myeloma and Non–Hodgkin's Lymphomas: Detection of P–Glycoprotein and Potential Circumvention by Addition of Verapamil to Chemotherapy," *J. Clin. Oncology*, 7(4):415–424, 1989.

Endicott et al., "The Biochemistry of P–Glycoprotein–Mediated Multidrug Resistance," *Annu. Rev. Biochem.*, 58:137–171, 1989.
Gottesman et al., "The Multidrug Transporter, a Double–edged Sword," *J. Biol. Chem.*, 263(25):12163–12166, 1988.
Holló et al., "Calcein Accumulation as a Fluorometric Functional Assay of the Multidrug Transporter," *Biochimica et Biophysica Acta*, 1191:384–388, 1994.
Homolya et al., "Fluorescent Cellular Indicators Are Extruded by the Multidrug Resistance Protein," *J. Biol. Chem.*, 268(29):21493–21496, 1993.
Juranka et al., "P–glycoprotein multidrug–resistance and a superfamily of membrane–associated transport proteins," *FASEB Journal*, 3:2583–2591, 1989.
Kamimoto et al., "The Function of Gp170, the Multidrug Resistance Gene Product, in Rat Liver Canalicular Membrane Vesicles," *J. Biol. Chem.*, 264(20):11693–11698, 1989.
Pastan et al., "Molecular manipulations of the multidrug transporter: a new role for transgenic mice," *FASEB Journal*, 5:2523–2528, 1991.
Raviv et al., "Photosensitized Labeling of a Functional Multidrug Transporter in Living Drug–resistant Tumor Cells," *J. Biol. Chem.*, 265(7):3975–3980, 1990.

(List continued on next page.)

*Primary Examiner*—Christopher S. F. Low
*Assistant Examiner*—Anish Gupta
(74) *Attorney, Agent, or Firm*—Keil & Weinkauf

(57) ABSTRACT

The invention features novel peptide derivatives called Reversins, and provides for their use in a method of reducing the activity of the multi-drug transporter protein MDR1 in order to overcome multidrug resistance in a mammal. The peptide derivatives are of the formula (I) $X^1_n\text{-}X^2\text{-}X^3(X^4)_n\text{-}X^5$, wherein n is 0 or 1, and each n is the same or different; $X^1$ is BOC, BOC-Asu, Z-Asu, benzyloxycarbonyl, Glu(OBzl)-OBzl, Trp-OMe, Trp-Phe-OMe, Phe-Trp-OMe, Phe-Phe-OtBu, Trp-Trp-OtBu, indoloacetyl, benzoyl, an alkylanine of 1–4 carbons, dibenzylamide, tryptamide, 1-aminoadamantine, aminomethylcyclohexane, indoline, phenylethylamide or dicyclohexylamide; $X^2$ is Glu(OBzl), Asp(OBzl), succinyl, O,O-dibenzoyltartaroyl, diphenoyl, muconyl, Thx, Cpa, Asu, Nal, Pen, Phg, Dbt, Lys(BOC), Lys(Z), Cys(Bzl), Thr(Bzl), Glu(OtBu), tert.-Leu, Leu, Nle, Pro, Phe, Tyr(Bzl), or Ser(Bal); $X^3$ is Asp, Asu, Lys, Glu, Trp, Thx, Cpa, Nal, Pen, Phg, Dbt, Glu(OtBu), tert.-Leu, Leu, Nle, Pro, Tyr, Phe, or Tyr(Bzl); $X^4$ is BOC-Glu(OBzl), Glu(OBzl), Asu, OBzl, Bzl, BOC, BOC-Lys(BOC), Z-Glu(OtBu), Asp(OBzl), Asp(OBz)-OBzl, benzyloxycarbonyl, O-(cyclo-hexyl), fluorenylmethyl ester, Glu(OtBu), Glu(OtBu)-OBzl, 1-amino-adamantine, aminomethylcyclohexane, indoline, phenylethylarnide, or dicyclohexylamide; and $X^5$ is OMe, OBzl, OtBu, Phe-OMe, -O-(cyclohexyl), Trp-OMe, (chlorophenyl)-isobutylamide, fluorenylmethyl ester, ONp, 1-aminoadamantane, aminomethylcyclohexane, indoline, phenylethylamide, or dicyclohexylamide.

9 Claims, 9 Drawing Sheets

OTHER PUBLICATIONS

Riordan et al., "Genetic and Biochemical Characterization of Multidrug Resistance," *Pharmac. Ther.*, 28:51–75, 1985.

Riordan et al., "Amplification of P-glycoprotein genes in multidrug-resistant mammalian cell lines," *Nature*, 316:817–819, 1985.

Sarkadi et al., "Expression of the Human Multidrug Resistance cDNA in Insect Cells Generates a High Activity Drug-stimulated Membrane ATPase," *J. Biol. Chem.*, 267(7):4854–4858, 1992.

Sarkadi et al., "Interaction of Bioactive Hydrophobic Peptides with the Human Multidrug Transporter," *FASEB Journal*, 8(10):766–770, 1994.

Schinkel et al., "Disruption of the Mouse mdr1a P-Glycoprotein Gene Leads to a Deficiency in the Blood-Brain Barrier and to Increased Sensitivity to Drugs," *Cell*, 77:491–502, 1994.

Sharma et al., "Peptide Transport by the Multidrug Resistance Pump," *J. Biol. Chem.*, 267(9):5731–5734, 1992.

Solary et al., "P-Glycoprotein Expression and In Vitro Reversion of Doxorubicin Resistance by Verapamil in Clinical Specimens From Acute Leukaemia and Myeloma," *Leukemia*, 5(7):592–597, 1991.

Tsuruo et al., "Circumvention of Vincristine and Adriamycin Resistance in Vitro and in Vivo by Calcium Influx Blockers," *Cancer Research*, 43:2905–2910, 1983.

Yoshimura et al., "Novel screening method for agents that overcome classical multidrug resistance in a human cell line," *Cancer Letters*, 50:45–51, 1990.

Organic Chemistry, Pine et al., 4$^{th}$ Ed., 1998, 803–809.

Cancer Letters, 50 (1990) 45–51, Shudo et al.

Cancer Res. 43, 2905–2910, Jun. 1983, Tsuruo et al.

Leukemia, vol. 5, No. 7, Jul. 1991, pp. 592–597, Solary et al.

Nature vol. 316, Aug. 1985, 817–819, Riordan et al.

Jrl. of Bio. Chem., vol. 267, No. 7, Mar. 5, 4854–4858, 1992, Sarkadi et al.

FASEB Jrl. vol. 8, Jul. 1994, 766–770, Sarkadi et al.

Cell, vol. 77, 1–20, May 20, 1994, Schinkel et al., pp. 1–12.

Jrl. of Bio. Chem. vol. 267, No. 9, Mar. 15, 1992, pp. 5731–5734, Sharma et al.

Pharmac. Ther. vol. 28, pp. 51 to 75, 1985, Riordan et al.

Jr. Bio. Chem., vol. 265, No. 7, Mar. 5, 1990, pp. 3975–3980, Raviv et al.

FASEB Jr., vol. 5, Aug. 1991, Pastan et al., pp. 1523–2538.

Jr. of Bio. Chem., vol. 264, No. 20, Jul. 15, pp. 11693–1698, 1989, Kaminoto et al.

FASEB Jrl., vol, e, Dec. 1989, Juranka et al., 2583–2592.

Jr. Bio. Chem. vol. 268, No. 29, Oct. 15, 1993, pp. 21493–21496, Homolya et al.

Biochimica et Biophysica Acta 1191, 1994, 384–388, Hollo et al.

Jr. of Bio. Chem. vol. 263, No. 25, Sep. 5, 1988, pp. 12163–12166, Gottesman et al.

Annu. Rev. Biochem. 1989, 58:137–71, Endicott et al.

Jrl. of Clinical Oncology, vol. 7, No. 4, Apr. 1989, pp. 415,424, Dalton et al.

Derwent, SU 1544778, Abstract.

\* cited by examiner

BOC-Asp(OBzl)-Lys(Z)-OtBu

COMPOUNDS FOR REVERSING DRUG RESISTANCE

BACKGROUND OF THE INVENTION

This invention relates to compounds for overcoming resistance that a patient may build to therapeutics.

Treatment of many diseases can be severely limited by resistance to the chosen therapeutic drug. For example, chemotherapy, while generally an effective treatment against human cancerous diseases, is hampered when a patient becomes resistant to the chemotherapeutic. In one special form of drug resistance, called "Multidrug Resistance," the cell becomes resistant not only to the chemotherapeutic being administered, but to a wide range of structurally and functionally unrelated drugs simultaneously (see Ford et al., *Pharmacological Reviews*, 42:155–199, 1992).

The cause of multidrug resistance is the appearance of an integral glycoprotein in the plasma membrane of the targeted cell, e.g., a tumor cell (FIG. 1). The protein functions as a multidrug transporter, and is variously called MultiDrug-Resistance 1 protein (MDR1), P-glycoprotein (pleiotropic-glycoprotein), Pgp, or P-170. MDR1 consists of 1280 amino acid residues, and contains 12 transmembrane segments and two nucleotide-binding domains. It strongly resembles prokaryotic and eukaryotic members of the so-called ABC (ATP Binding Cassette) transporters, or traffic ATPases (see Endicott et al., *Annu. Rev. Biochem.* 58:137–171, 1989; Higgins, *Annu. Rev. Cell. Biol.* 8:67–113, 1992).

MDR1 naturally functions to, and is highly expressed in tissues normally responsible for, extruding toxic materials and waste-products from cells (e.g., lung, kidney, and liver), and secretes hydrophobic compounds from exocrine or endocrine glands (Gottesman et al., *J. Biol. Chem.* 263:12163–12166, 1988; Higgins et al., supra). Consistent with its natural function, MDR1 catalyses an ATP-dependent extrusion of various cytotoxic drugs from the cell, e.g., vinca alkaloids, anthracyclines, and other natural antibiotics, thereby maintaining their cellular level at a subtoxic concentration. Thus, when expressed by tumor cells, MDR1 expels cytotoxic chemotherapeutic agents, and thus allows the tumor cell to survive anticancer treatments even at high drug doses. At the same time, "ordinary" cells, having no such extrusion mechanism, may receive a lethal drug exposure. Tumors developing from tissues normally expressing the MDR1 protein often show a primary drug resistance, while in other tumors a secondary drug resistance may develop after chemotherapy.

The phenomenon of multidrug resistance is not limited to tumor cells. MDR1 and its homologues are expressed in a wide variety of cell-types, including parasitic protozoa. Consequently, overexpression of a member of the MDR1 family of proteins creates obstacles to a wide variety of parasitic diseases, including malaria, African sleeping sickness, and others (Campbell et al., *Chemotherapy of Parasitic Diseases*, Plenum Press:NY, 1986; Henderson et al., *Mol. Cell. Biol.* 12:2855–65, 1992). MDR1 is also expressed by endothelial cells of human capillary blood vessels at the blood-brain barrier and blood-testis barrier (Ford et al. supra, at 159).

It is known that verapamil, a drug that blocks voltage-dependent calcium channels, stimulates the activity of MDR1-bound ATPase at a concentration of 1 to 20 μM but inhibits it as a concentration above 100 μM (Sarkadi et al. *J. Biol. Chem.* 267:4854–4858, 1992). While between these concentrations verapamil blocks the extrusion of antitumor drugs, its high toxicity severely limits its clinical use (Solary et al. *Leukemia* 5:592–597, 1991; Dalton et al. *J. Clin. Oncology* 7:415–418, 1989).

In SU-A-1544778, Golovina, T. N. et al describe the preparation of different peptides one of which, BOC-Leu-Tyr-OMe is structurally close to the peptides provided by the present invention. Nevertheless, no hints on the possible biological activity of said peptide are disclosed.

SUMMARY OF THE INVENTION

The invention generally features chemical compositions which reduce or overcome multidrug resistance in a mammal, e.g., a human, and in microorganisms causing disease in a mammal. The compounds, called "Formula (I)" compounds, or "Reversins", are hydrophobic peptide derivatives which effectively compete with cytostatic drugs on the MDR1 protein, thus reducing or eliminating drug resistance.

"Multi-drug resistance", as used herein, refers to the ability of cells to develop resistance to a broad range of structurally or functionally unrelated drugs. This occurs by outward transport of the drug from the cell, the transport being mediated by the MDR1 glycoprotein or its homologues. The term "multidrug resistance" also applies to the cross-resistance between drugs which is adversely affected by the Reversin compounds of the invention (see below). Preferably, "multidrug resistance" refers to the state which is dependent on expression or overexpression of the MDR1 protein or its homologues, and/or on gene amplification of human mdr1 or its homologues. Both primary and secondary multidrug resistance are included. Where the drug resistance is "primary" the cell has experienced no previous exposure to a member of the group of drugs, yet exhibits inherent resistance to them. Where drug resistance is "secondary", the cell has been exposed to only one drug, or to only a subset of two or more, but not necessarily to the whole, group of drugs affected by cross-resistance.

The compounds of the invention, hereafter called "Reversins", are of formula (I):

$$X^1{}_n\text{-}X^2\text{-}X^3\text{-}(X^4)_m\text{-}X^5 \qquad (I)$$

wherein n and m are 0 to 1;

$X^1$ is BOC, BOC-Asu, Z-Asu, benzyloxycarbonyl, Glu(OBzl)-OBzl, Trp-OMe, Trp-Phe-OMe, Phe-Trp-OMe, Phe-Phe-OtBu, Trp-Trp-OtBu, indoloacetyl, benzoyl, an alkylamine of 1–4 carbons, dibenzylamide, tryptamide, 1-amino-adamantine, aminomethylcyclohexane, indoline, phenylethylamide or dicyclohexylamide;

$X^2$ is Glu(OBzl), Asp(OBzl), succinyl, O,O-dibenzoyltartaroyl, diphenoyl, muconyl, Thx, Cpa, Asu, Nal, Pen, Phg, Dbt, Lys(BOC), Lys(Z), Cys(Bzl), Thr(Bzl), Glu(OtBu), tert.-Leu, Leu, Nle, Pro, Phe, Tyr(Bzl), or Ser(Bzl);

$X^3$ is Asp, Asu, Lys, Glu, Trp, Thx, Cpa, Nal, Pen, Phg, Dbt, Glu(OtBu), tert.-Leu, Leu, Nle, Pro, Tyr, Phe; or Tyr(Bzl);

$X^4$ is BOC-Glu(OBzl), Glu(OBzl), Asu, OBzl, Bzl, BOC, BOC-Lys(BOC), Z-Glu(OtBu), Asp(OBzl), Asp(OBz)-OBzl, benzyl-oxycarbonyl, O-(cyclo-hexyl), fluorenyl-methyl ester, Glu(OtBu), Glu(OtBu)-OBzl, 1-amino-adamantine, amino-methylcyclohexane, indoline, phenylethylamide, or dicyclohexylamide; and $X^5$ is OMe, OBzl, OtBu, Phe-OMe, -O-(cyclohexyl), Trp-OMe, (chlorophenyl)-isobutylamide, fluorenylmethyl ester, ONp, 1-aminoadamantane, aminomethylcyclohexane, indoline, phenylethylamide, or dicyclohexylamide, with the proviso that said formula (I) is not BOC-Leu-Tyr-OMe.

Formula (I) compounds containing amino acids with either the L or D configuration fall within the scope of the invention.

Side chain protecting groups of amino acids may be substituted by one or more halogen atoms, e.g., chloro-Z, or bromo-Z. Such blocking groups are known. A benzyl ester group can be substituted by one or more nitro groups in the second or fourth position of the benzene ring.

The abbreviations used herein are known to those skilled in the art (see, e.g., *J. Biol. Chem.* 241:527, 1966; *J. Biol. Chem.* 247:977 1972; hereby incorporated by reference). Other abbreviations used herein are as follows:

| AM: | acetoxymethyl ester |
|---|---|
| Asu: | aminosuccinic acid or aminosuccinoyl |
| BOC: | tert.-butyloxycarbonyl, |
| Bzl: | benzyl, |
| Cpa: | 4-chlorophenylalanyl, |
| Cys: | cysteinyl, |
| Dbt: | dibromotyrosyl, |
| DBTA: | dibenzoyltartaroyl, |
| DCC: | dicyclohexylcarbodiimide, |
| DCU: | dicyclohexylurea, |
| DIC: | diisopropylcarbodiimide, |
| DMF: | dimethylformamide |
| HPLC: | high pressure liquid chromatography, |
| MDR1: | product of multidrug resistance gene, |
| Me: | methyl, |
| Nal: | naphthylalanyl, |
| Nle: | norleucyl, |
| m.p.: | melting point, |
| OPFP: | pentailuorphenyl |
| $ON_p$: | p-nitrophenyl |
| Pen: | penicillinalanyl, |
| Phe: | phenylalanyl, |
| Phg: | phenylglycyl, |
| Pro: | prolyl, |
| $R_f$: | retention factor, |
| SUC: | succinyl, |
| TEA: | triethylamine, |
| THF: | tetrahydrofuran, |
| Thr: | threonyl, |
| Thx: | thyroxyl, |
| TLC: | thin layer chromatography, |
| Trp: | tryptophyl, |
| Z: | benzyloxycarbonyl. |

As preferred embodiments of the invention, $X^1$ can be BOC, Glu(OBzl)-OBzl, Z, or (D-Phe-Trp-OMe); $X^2$ can be Asp(OBzl), succinyl, Glu(OBzl), or DBTA; $X^3$ can be Lys, Glu, Asp, or Phe; $X^4$ can be Z, OBzl, BOC-Glu(OBzl), BOC-Lys(BOC), or Z-Glu(OtBu); or $X^3$ and $X^4$ in combination can be Lys[BOC-Glu(OBzl)]; and $X^5$ can be OtBu, OBzl, OMe, or Trp-OMe.

Preferred formula (I) compounds of the invention include, but are not limited to, the peptide derivatives BOC-Asp(OBzl)-Lys(Z)-OtBu (Reversin 121); succinylbis[Glu(OBzl)-OBzl]; Z-D-Glu(OBzl)-D-Asp(OBzl)-OBzl; DBTA-bis(D-Phe-Trp-OMe); DBTA-[Glu(OBzl)$_2$]$_2$; $N^\alpha, N^\epsilon$-bis[BOC-Glu(Bzl)]-Lys-OMe (Reversin 205); BOC-Tyr(Bzl)-Tyr(Bzl)-OMe; BOC-D-Ser(Bzl)-Lys(Z)-OtBu; BOC-Glu(OBzl)-Lys(Z)-OtBu; BOC-Glu(OBzl)-Lys(Z)-OMe; $N^\alpha, N^\epsilon$-bis[BOC-Lys(BOC)]-Lys-OMe; or $N^\alpha, N^\epsilon$-bis[Z-Glu(OtBu)]-Lys-OMe.

Any of the various compounds of the invention can be combined with a pharmaceutically acceptable carrier or an adjuvant. The various compounds of the invention can also be combined with a drug, e.g., a chemotherapeutic, antiparasitic, or antibiotic drug, for convenient co-administration of the Reversin compound and the drug to a patient. The Reversin molecule can, in addition to inhibiting MDR1 activity, also act as a adjuvant to enhance the activity of the drug. As used herein, a "drug", includes a medication, a pharmaceutical, or a substance which is intended for use in diagnosis, cure, mitigation, treatment, or prevention of disease, or which is generally intended to affect the structure or the function of the body of a mammal.

The invention also includes a method of preparing any of the various formula (I) compounds of the invention. The method involves providing a combination of one or more of $X^1{}_n$, $X^2$, $X^3$, $X^4{}_n$, $X^5$, or $X^1X^2$ in a solution, e.g., by dissolving the combination, e.g., one or more of $X^1{}_{n,X}{}^2$, $X^3$, $X^4{}_n$, $X^5$, or $X^1X^2$, in a solution; cooling the solution; adjusting the pH of the solution to the neutral range, e.g., a pH of 4–8, preferably pH 6–8, or between pH 7 and 8, inclusive; and purifying the formula (I) compound from the solution. By "purifying" is meant extracting, filtering, evaporating, precipitating, washing, recrystallizing, isolating by chromatography, or any other means of isolating the desired Reversin compound from the reaction mixture. The method can further include an additional purification step to remove any impurities from the final product, e.g., a gel filtration step, or a chromatographic step (see Methods, below). The method can also include, or further include, a step of active ester coupling, or a step of dicyclohexylcarbodiimide condensation characterized by the following parameters: cooling by ice-water, 10% excess of DCC, pH adjusted between 7–8 with tertiary base (e.g. triethylamine, N-methylmolpholine, diisopropyl-ethylamine). In certain cases 1-hydroxybenzotriazole additive is used for activation and to avoid possible racemization (W. Lonig et al. *Chem Ber.* 103:2024, 1970, hereby incorporated by reference).

The invention also includes a method of reducing the activity of a multidrug transporter protein or its homologues in a mammal. The method involves administering to the mammal an amount of any of the various formula (I) compounds of the invention in a therapeutically effective amount. The method of reducing the activity of MDR1 can be used to lower resistance to a drug, where the drug includes one or more, e.g., at least one, two, or three drugs, which are chemotherapeutic drugs, antiparasitic drugs, or antibiotic drugs. By "mammal" is meant a human, a domesticated animal, e.g., a cat or a dog, or an agricultural animal, e.g., a cow, pig, sheep, horse, or poultry. A "chemotherapeutic drug" includes any drug intended to target and kill a tumor cell, e.g., neoplastic, malignant, or benign tumor cell, in a mammal. An "antiparasitic drug" includes a drug intended to target the agent of a parasitic infection, e.g., ascaris, enterobium, hookworm, threadworm, tapeworm, schistosomes, whipworm, protozoa, e.g., intestinal or extraintestinal amebas, giardia, malaria, toxoplasma, or trichomonas. An "antibiotic drug" includes substances which inhibit or kill fungal or bacterial microorganisms, e.g., actinomycin. Examples of drugs within the scope of the invention include, but are not limited to, the substances listed in Table 1, as well as any chemotherapeutic, antiparasitic, and antibiotic drugs which clinically elicit, or whose therapeutic effects are limited by, primary or secondary multidrug resistance caused by MDR1 (Ford et al. supra; hereby incorporated by reference).

Cytotoxic drugs which are extruded by the MDR1 protein or its homologues include, but are not limited to, the compounds shown in Table 1.

TABLE I

Drugs exported by the MDR1 protein

| | Examples |
|---|---|
| Anti-Cancer Drugs | |
| Vinca alkaloids | vinblastine, vincristine vindesine |
| Anthracyclines | doxorubicin, daunorubicin epirubicin |
| Epipodophyllotoxins | etoposide |
| Antibiotics | actinomycin D |
| Others | mitomycin C, taxol, topotecan, mithramycin |
| Other cytotoxic agents | |
| Anti-microtubule drugs | colchicine, podophyllotoxin |
| Protein Synthesis inhibitors | puromycin, emetine |
| DNA intercalators | ethidium bromide |
| Toxic peptides | valinomycin, gramicidin D,N-acetyl-leucyl leucyl-norleucinal (ALLN) |

The method of reducing the activity of a MDR1 protein or its homologues in a mammal is also used to facilitate administration of a drug through membranes which exclude various substances from a given type of cell or tissue. In particular, Reversins can be used to aid transport of a drug through the blood-brain barrier, or through the blood-testis barrier. By "blood-brain barrier" and "blood-testis barrier" is meant the endothelial lining of cells that are selectively permeable or impermeable to substances circulating outside of the brain or testis, respectively.

A "multidrug transporter protein" (MDR1), as used herein, refers to a glycoprotein present on the membrane of many cell types which acts to extrude various substances from the cell. In humans, MDR1 is commonly referred to as the P-glycoprotein, P-170, or Pgp, and is encoded by the mdr1 gene. Also included are homologues of MDR1 which are members of the MDR1 family of proteins in other organisms, e.g., prokaryotes or lower eukaryotes, e.g., bacterial, yeast, fungal, parasitic organisms, or other organisms that take up residence within a mammalian body. Homologues within the MDR1 family of proteins perform the same function as MDR1 for cells of the other organisms, i.e., by transporting hydrophobic cytotoxic compounds out of the cell. Generally, the method of the invention is intended to inhibit the activity of members of the MDR1 protein family which are shown by the assays below to be affected by a Reversin compound.

A "therapeutically effective amount", as used herein, refers to an amount that is effective at reducing the activity of the multidrug transporter protein; an amount that is effective at lowering resistance of the mammal to a drug or to a group of drugs; or an amount that is effective for facilitating absorption of a drug through the blood brain barrier. An "effective amount" can be calibrated by the assays below. By "facilitating" is meant enhancing the overall amount of the drug that is absorbed, or the fraction of the drug that is absorbed.

As used herein, the term "reducing" means either partially or completely inhibiting MDR1 activity. By "reducing" is also meant decreasing, lowering, or overcoming the effects of drug or multidrug resistance, so that less drug is transported from the target cell, or so that a greater concentration of drug accumulates within the cell. As used herein, the term "reducing" encompasses both treating and preventing the occurrence of drug, e.g., multidrug, resistance in a mammal.

The level of MDR1 activity present in a cell or in a target tissue is measured by the assays provided below. This in turn permits accumulation of drug at higher concentrations in the cell than would be possible in the absence of the Reversin compound.

Other features and advantages of the invention will be apparent from the following detailed description and from the claims.

DETAILED DESCRIPTION

We first briefly describe the drawings.

Drawings

Figure 7:
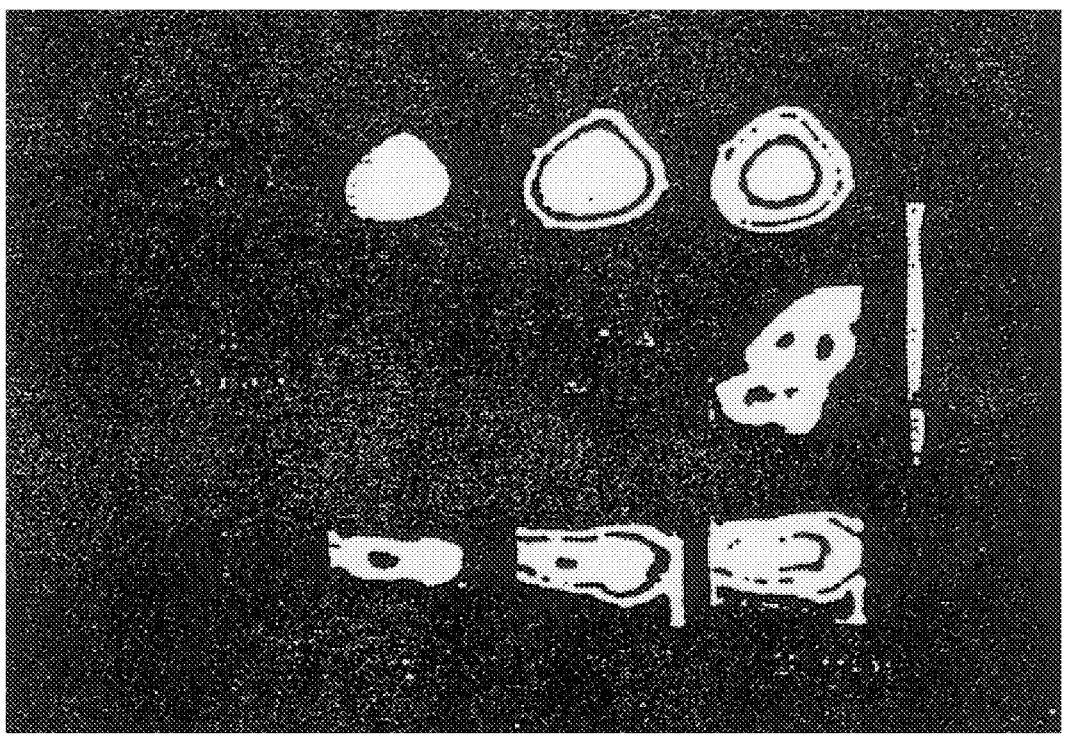

FIG. 7 is a photograph showing the effect of verapamil on dye loading in MDR1-expressing fibroblasts using single-cell imaging for fluorescent dye uptake. The upper panel shows control NIH 3T3 cells; middle and lower panels show MDR1-3T3 cells. In the lower panel the medium also contained 25 $\mu$M verapamil.

Figure 8:
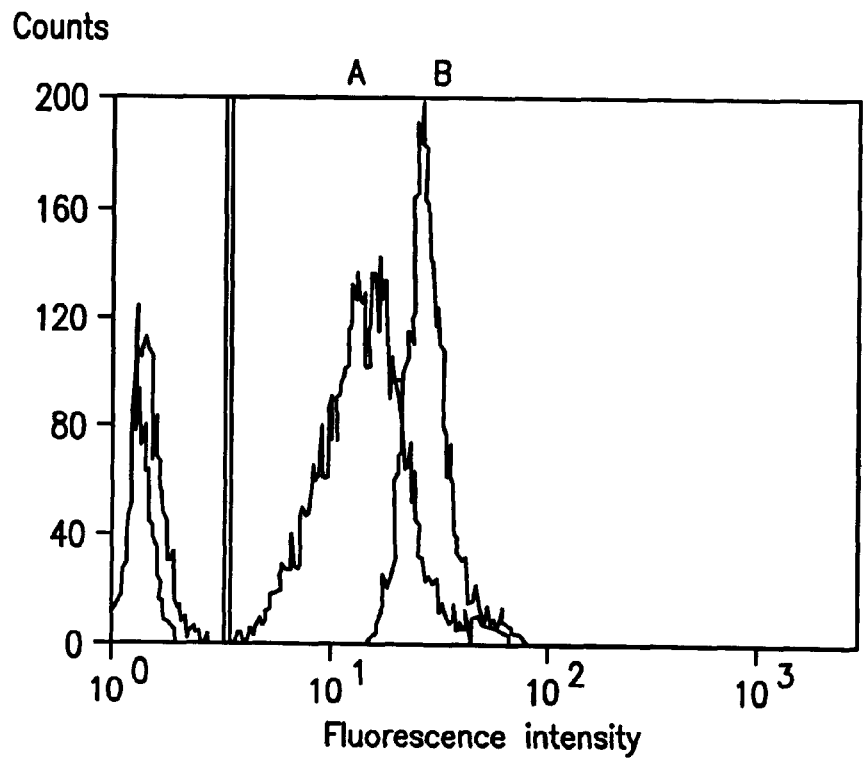

FIG. 8 is a graphic illustration of the fluorescent dye uptake of control cells (A) versus fluorescent dye uptake in the presence of 5 $\mu$M Reversin 205 (B).

Figure 9:
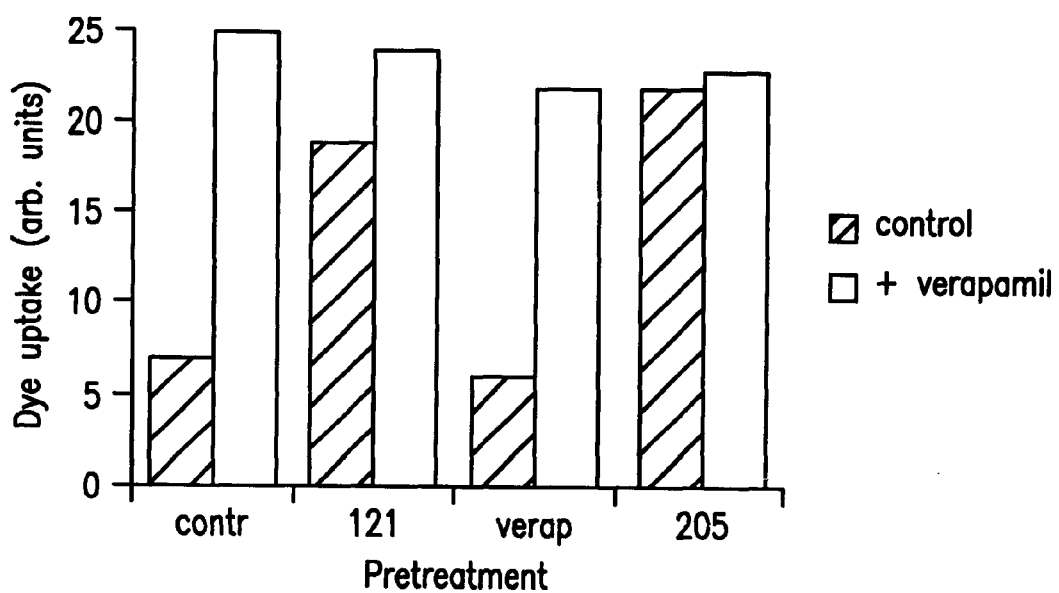

FIG. 9 is a bar graph showing the effect of various pretreatments and washings on fluorescent dye uptake into 3T3-MDR cells.

Figure 10A:
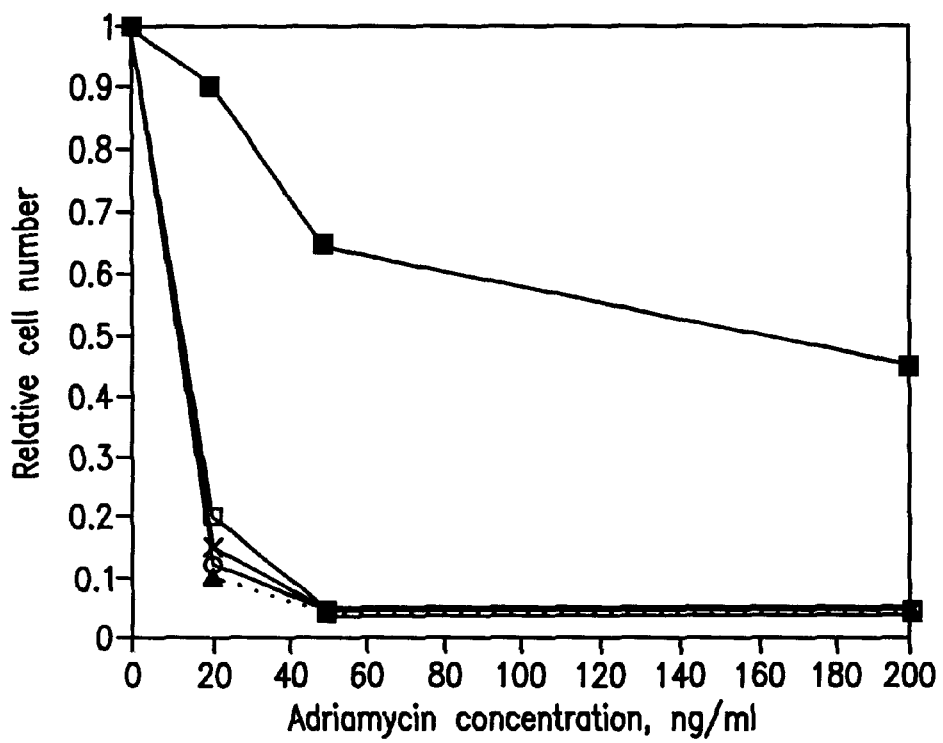
Figure 10B:
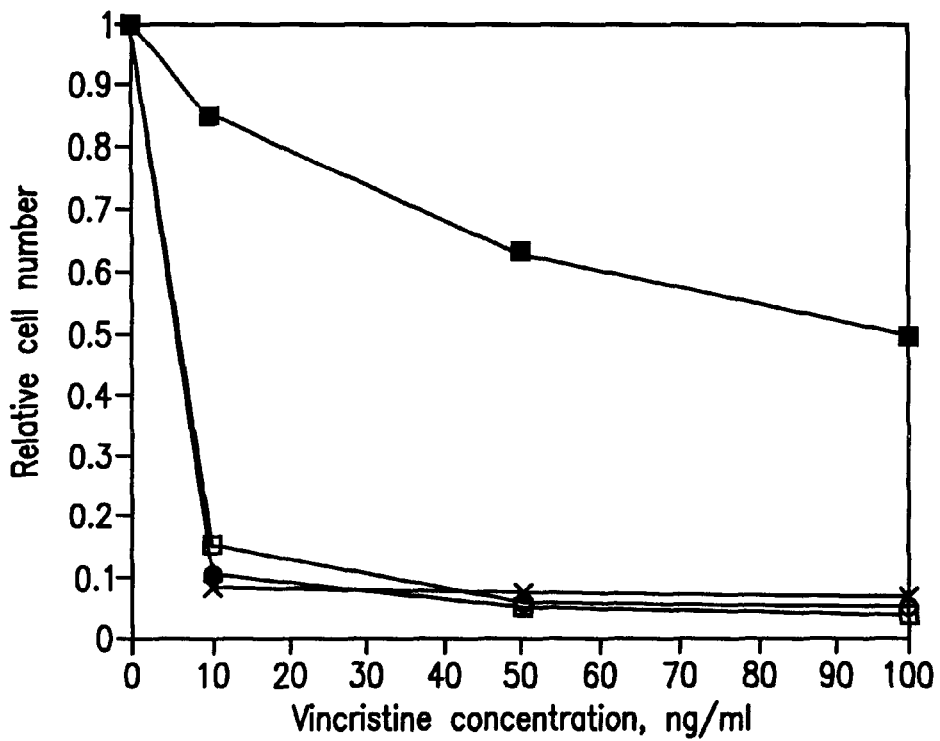

FIGS. 10A and 10B are graphic illustrations of the effect of Reversin 205 and verapamil on drug-sensitive and multidrug resistant cultured human tumor cells (K562) treated with adriamycin (A) or vincristine (B). ─▱─K562 control, ─+─K652+5 $\mu$MR, ─✳─K562+10 $\mu$M Verap, ─■─K562 MDR, ─▶─MDR+5 $\mu$MR, ─▱─K562 MDR+10 $\mu$MV.

Figure 11A:
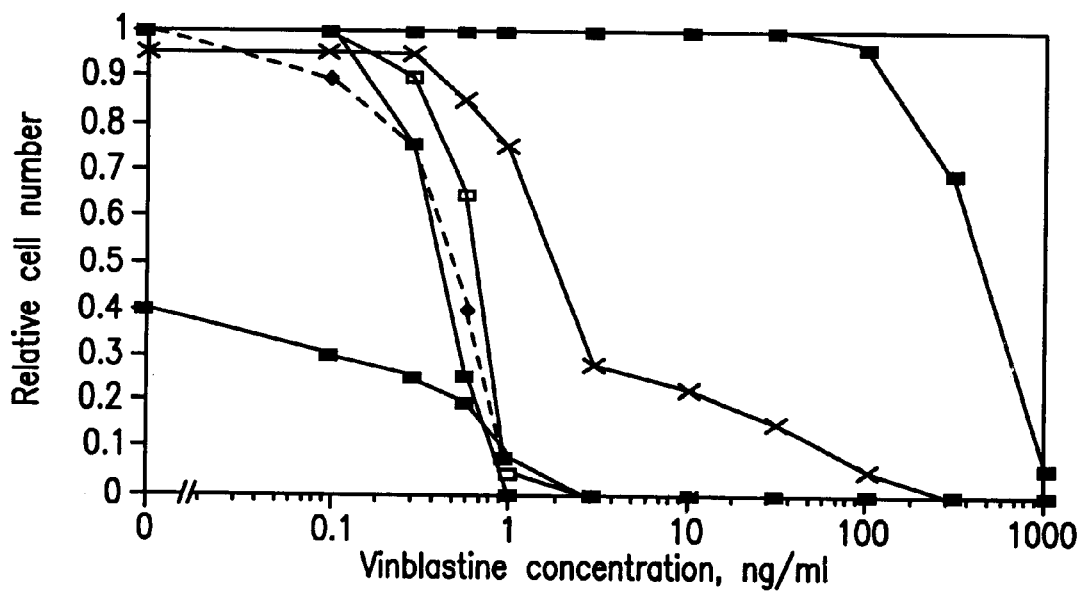
Figure 11B:
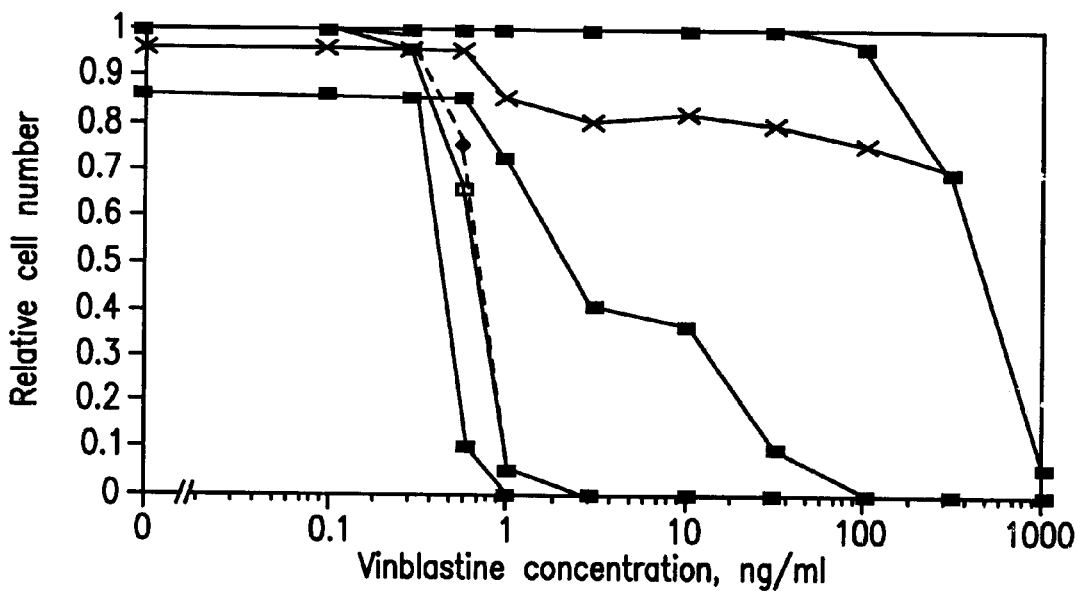

FIGS. 11A and 11B are graphic illustrations of the effect of Reversins 121 (A) and 205 (B) on the vinblastine-sensitivity of drug-sensitive (KB3) and multidrug-resistant (KBV1) cultured human tumor cells. ─▱─KB3 control, ─+─KB3+2 ug/ml R, ─✳─KB3 +10 ug/ml R, ─■─KBV1 control, ─▶─KBV1+2 ug/ml R, ─▱─KBV1+10 ug/ml R.

REVERSIN COMPOUNDS

The aim of the present invention is to provide chemical reversing agents, or chemosensitizers, to address the clinical problem of multidrug resistance. Toward this end applicants designed a set of novel hydrophobic peptide-based molecules called Reversins.

Reversins effectively inhibit expulsion of therapeutic drugs. They are effective at low concentration, non-toxic, and reversible. Reversins also leave the organism without adverse side effects, and in some cases even enhance the activity of the drug therapy itself. They can be prepared in high purity, in large quantities, and at relatively low cost. Reversins are especially advantageous for preventing resistance against anticancer drugs, without causing serious side-effects in other tissues, and without irreversibly disrupting the important natural physiological function of the MDR1 transport protein itself.

Methods of Preparation

Figure 1:
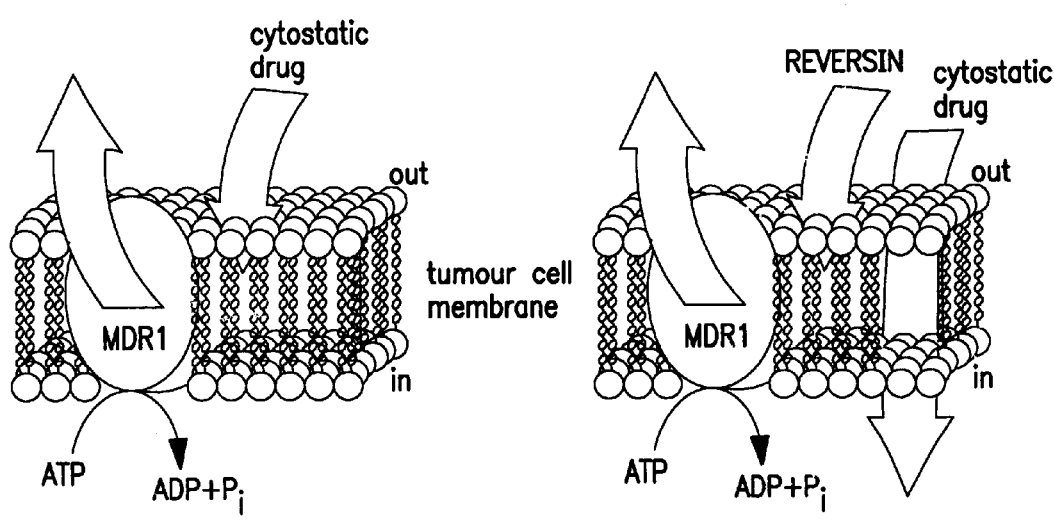
FIG. 1 is a schematic illustration of the MDR1 protein in its membrane environment.
Figure 2:
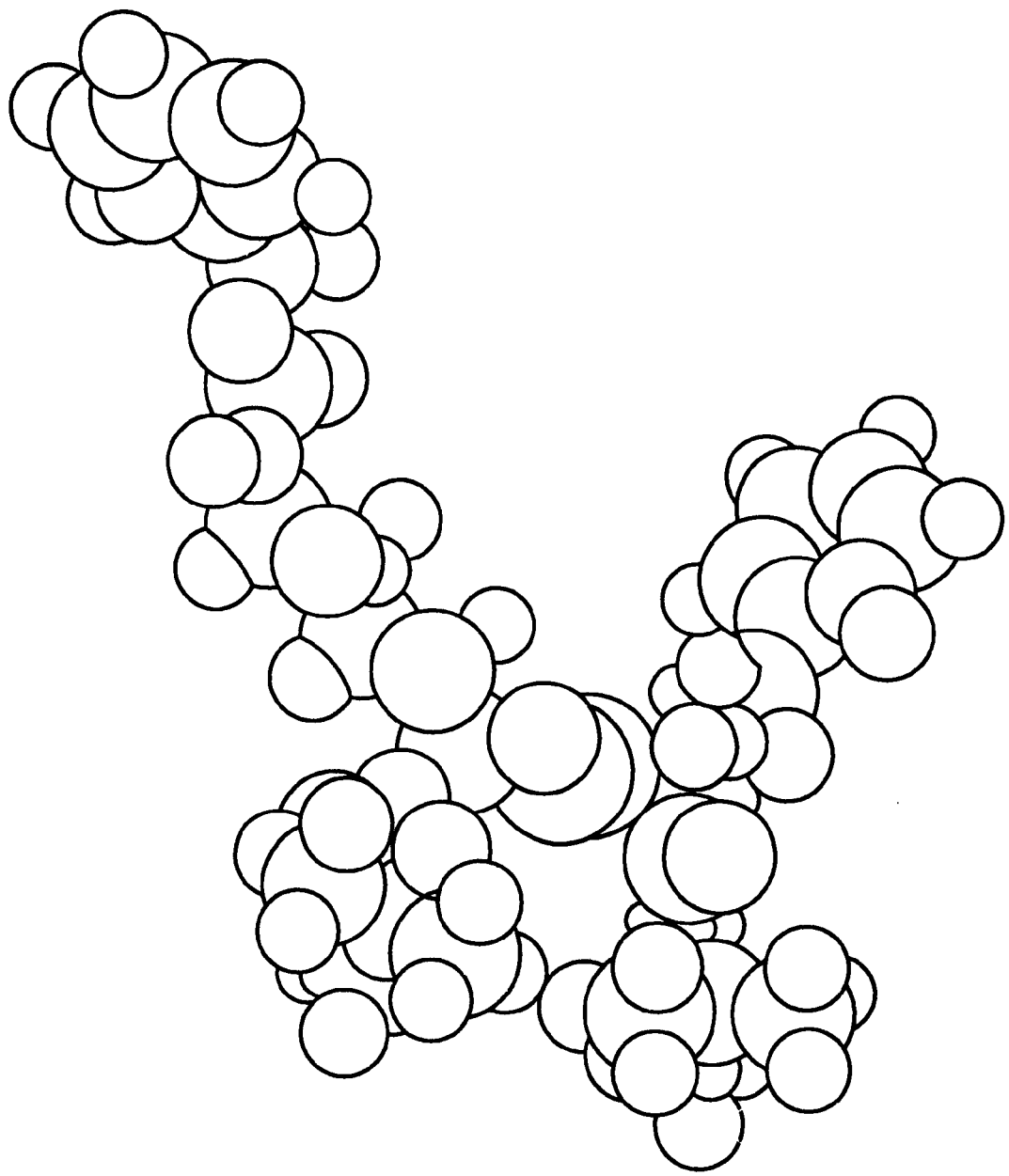
FIG. 2 is a computer-generated illustration of the secondary structure of the Reversin 121 molecule, BOC-Asp (OBzl)-Lys(Z)-OtBu.

Reversins are peptide derivatives consisting of naturally occurring L amino acids with bulky aromatic or alkyl groups, and carboxamide or carboxylic acid ester groups. The hydrophobic side-chains of the molecules enhance their interaction with the MDR1 transporter for which they are a substrate. The overall size of the molecule also influences this interaction. Dipeptides and tripeptides are preferred. A computer-analyzed secondary structure of a preferred dipeptide, Reversin 121, is illustrated in FIG. 2.

In general, Reversins are synthesized by an appropriate fragment condensation reaction, depending on the chemical character of the amino acid moiety in the compound being prepared. Reversins are synthesized by traditional stepwise condensation methods (The Peptides: Methods of peptide synthesis, Eds. E. Schoder, K. Lubke, Acad. Press, NY, 1966; The Peptides: Analysis, synthesis and biology, Ed. by E. Gross, J. Meienhofer, Acad. Press, NY 1979, each hereby incorporated by reference), or by automated solid-phase peptide synthetic methods, which are relatively large-scale and inexpensive. Reversins are also prepared by methods known to those of ordinary skill in the art, and as exemplified by Examples 1–12, below.

Each of the Examples 1–12, below, are prepared from amino acids that were protected to a desired grade. The starting materials are dissolved in apolar solvents, e.g., DMF, acetonitril, or DMSO. Condensation reactions are performed in solution, or by passage of the solution over a solid-phase column. The solution is cooled, for example to 0–10° C., and the pH is adjusted to the neutral range with, e.g., triethylamine, N-methylmorpholine, trimethyalmine, or diisopropylethylamine, and the product is allowed to form slowly, e.g. by stirring overnight. Finally, the Reversin compound is purified from the reaction mixture by, e.g., filtration of the precipitate, or by evaporating away the mother liquor, and the product is washed.

The final products can receive additional purification in order to remove any contaminants from the Reversin compound. The final purification step can include one or a combination of the following procedures: ethyl acetate; gel filtration; preparative high pressure liquid chromatography (HPLC); medium pressure column chromatography; or silica gel column chromatography. The purity of the peptides obtained is determined by thin layer chromatography (TLC) analysis.

In the examples that follow, $R_f$ values were obtained by TLC on Kiesel gel sheets (DC Alufolien Merck) using the following solvent mixtures (in the examples the solvent mixtures will be identified by the numbers listed below):

(1) acetone:toluene, 1:1

(2) chloroform:acetic acid:benzene, 85:10:5

(3) acetic acid:benzene, 1:7

(4) ethyl acetate:pyridine:acetic acid:water 240:20:6:11.

In general, Reversins are only slightly soluble in water (maximum solubility is about 10 µg/ml), while freely soluble in dimethyl sulfoxide (DMSO), glycerol, or ethanol. When testing a Reversin in an in vitro cellular screening assay, the presence of serum in the culture media increases the solubility of the Reversin.

The following non-limiting examples are provided to illustrate methods of preparing the Reversin compounds of the invention.

EXAMPLE 1

Preparation of BOC-Asp(OBzl)-Lys(Z)-OtBu (Reversin 121)

After dissolving 1 mmol of BOC-Asp(OBzl)-OH amino acid derivative (mole wt.=323) in 50 ml of DMF, 1.1 mmoles of DCC (mole wt.=206) and then 1 mmole of N6-carbobenzoxylysine tert.-butyl ester hydrochloride (mole wt.=371) were added while stirring and cooling with ice water. The pH value of the reaction mixture was adjusted to 7–8 with triethylamine and the mixture was stirred at room temperature overnight. The precipitate was filtered off and the mother liquor was evaporated. After taking up the residue in 150 ml of ethyl acetate, the extract was washed three times with 120 ml of 10% citric acid solution each, then three times with saturated sodium hydrogen carbonate solution, and finally three times with saturated saline solution. After drying the ethyl acetate phase over anhydrous sodium sulfate and filtering off the drying agent, the organic phase was evaporated and the residue was recrystallized from 30% alcohol to give the title product. m.p.: 128–129° C., $R_f$ (4)=0.9. The possible conformation of Reversin 121 is shown in FIG. 2.

The molecular mass of Reversin 121 is 641.5.

EXAMPLE 2

Preparation of succinyl-bis[Glu(OBzl)-OBzl]

To a solution containing 1 mmole of dibenzyl glutamate hydrochloride (mole wt.=362) in 50 ml of DMF, 0.5 mmole of bis(pentafluorophenyl) succinate was added while stirring and cooling with ice water. The pH value of the reaction mixture was adjusted to between 7 and 8 with triethylamine, and the mixture was stirred at room temperature overnight. Then the precipitate was filtered off, the mother liquor was evaporated and the residue was taken up in 150 ml of ethyl acetate. The organic solution was successively washed three times with 120 ml of 10% citric acid solution each, three times with saturated sodium hydrogen carbonate solution, and finally with saturated saline solution. After drying the ethyl acetate the phase over anhydrous sodium sulfate and filtering off the drying agent, the organic phase was evaporated, and the evaporation reside was recrystallized from aqueous alcohol to give the white crystalline title product, m.p.: 106–107° C., $R_f$ (4)=0.9.

EXAMPLE 3

Preparation of Z-D-Glu(OBzl)-D-Asp(OBzl)-OBzl

To a solution containing 1 mmol of the amino acid derivative Z-D-Glu(OBzl)-OH (mole wt.–371) in 50 ml of DMF, 1.1 mmoles of DCC and then 1 mmol of H-D-Asp (OBzl)-OBzl hydrochloride (mole wt.–349) were added while stirring and cooling with ice water. The pH value of the reaction mixture was adjusted to between 7 and 8 with triethylamine, and the mixture was stirred at room temperature overnight. After filtering off the precipitate, the mother liquor was evaporated, and the residue was taken up in 150 ml of ethyl acetate. The organic solution was successively washed three times with 120 ml of 10% citric acid solution each, three times with saturated sodium hydrogen carbonate solution, and finally with saturated saline solution. After drying the ethyl acetate phase over anhydrous sodium sulfate, the drying agent was filtered off and the organic phase was evaporated to give the title compound as a slightly yellow crystalline product. $R_f(4)=0.9$.

EXAMPLE 4

Preparation of DBTA-bis(D-Phe-Trp-OMe)

To a solution containing 1 mmole of the dipeptide hydrochloride D-Phe-Trp-OMe (mole wt.=401.8) in 50 ml of DMF, first 1.1 mmoles of DCC, and then subsequently 0.5 mmole of DBTA-(OPFP)$_2$ active ester (mole wt.=696), were added while stirring and cooling with ice-water. The pH value of the reaction mixture was adjusted to between 7 and 8 with triethylamine and the mixture was stirred at room temperature overnight. Then, the precipitate was filtered off, the mother liquor was evaporated, and the residue was taken up in 150 ml of ethyl acetate. The organic solution was successively washed three times with 120 ml of 10% citric acid solution each, 3 times with saturated sodium hydrogen carbonate solution, and finally three times with saturated saline solution. After drying the ethyl acetate phase over anhydrous sodium sulfate and filtering off the drying agent, the organic phase was evaporated to obtain the title compound as a foam-like amorphous evaporation residue. m.p.: 79–80° C., $R_f(4)=0.9$.

EXAMPLE 5

Preparation of DBTA-[Glu(OBzl)$_2$]$_2$

To a solution containing 1 mmole of the active ester DBTA-(OPFP)$_2$ (mole wt.=696) in 50 ml of DMF, 2 mmoles of Glu(OBzl)$_2$ tosylate (mole wt.–500) and then 0.28 ml (2 mmoles) triethylamine, were added while stirring and cooling with ice water. The pH value of the reaction mixture was adjusted to between 7 and 8 with triethylamine and the mixture was stirred at room temperature overnight. Then, the precipitate was filtered off and after evaporating the mother liquor the residue was taken up in 150 ml of ethyl acetate. The organic solution was successively washed three times with 120 ml of 10% citric acid solution each, three times with saturated sodium hydrogen carbonate solution, and finally three times with saturated saline solution. After drying the ethyl acetate phase over anhydrous sodium sulfate, the drying agent was filtered off and the organic phase was evaporated to give the title compound as an oily residue. $R_f(4)=0.9$.

EXAMPLE 6

Preparation of N$^\alpha$, N$^\epsilon$-bis[BOC-Glu(OBzl)]-Lys-OMe (Reversin 205)

Method A: To a solution containing 1 mmol of the amino acid derivative BOC-Glu(OBzl)-OH (mole wt.=337) in 50 ml of DMF, 1.1 mmoles of DCC and 1 mmoles of the amino acid derivative Lys-OMe dihydrochloride (mole wt.=228) were added while stirring and cooling in ice water. After adjusting the pH value to between 7 and 8 with triethylamine, the reaction mixture was stirred at room temperature overnight. Then, the precipitate was filtered off and the mother liquor was evaporated. The residue was taken up in 150 ml of ethyl acetate and successively washed three times with 120 ml of 10% citric acid each, three times with saturated sodium hydrogen carbonate solution, and finally three times with saturated saline solution. After drying the ethyl acetate phase over anhydrous sodium sulfate, the drying agent was filtered off and the organic phase was evaporated. After recrystallizing the evaporation residue from the aqueous alcohol, the title compound was obtained as a slightly yellow crystalline product. m.p.: 79–81° C., $R_f(1)=0.7$, $R_f(4)=0.95$.

Method B: A second method of preparing N$^\alpha$, N$^\epsilon$-bis [BOC-Glu(OBzl)]-Lys-OMe is according to the procedure of Example 11, except that 5.03 g of the amino acid active ester BOC-Glu(OBzl)-OPFP was used as the starting material, and the other constituents were used in the amounts of 1.15 g of Lys-OMe dihydrochloride, 20 ml of DMF and 1.38 ml of triethylamine.

The molecular mass of Reversin 205 is 875.5.

EXAMPLE 7

Preparation of BOC-Tyr(Bzl)-Tyr(Bzl)-OMe

To a solution containing 986 mg of the amino acid derivative BOC-Tyr(Bzl)-ONp (mole wt.=491) in 50 ml DMF, first 682 mg of H-Tyr(Bzl)-OMe. OMe hydrochloride salt (mole wt=384), and then 0.28 ml triethylamine were added while stirring and cooling with ice water. The pH value of the reaction mixture was adjusted to between 7 and 8 with triethylamine, and the mixture was stirred at room temperature for 24 hours. After evaporating the mother liquor the residue was taken up in 50 ml of ethyl acetate. The organic solution was successively washed three times with 2N KHSO$_4$ solution, three times with saturated sodium hydrogen carbonate solution, and three times with saturated saline solution. After drying the ethyl acetate phase over anhydrous sodium sulfate, the drying agent was filtered off. The organic phase was evaporated to give an oil which can be crystallized from the mixture of ethanol:water (7:3) to obtain the title compound. $R_f(1):0.95$; $(R_f(4):0.9$; m.p.= 161–163° C.

EXAMPLE 8

Preparation of BOC-D-Ser(Bzl)-Lys(Z)-OtBu

To a solution containing 10 mmoles of the amino acid derivative BOC-D-Ser(Bzl)-OH (mole wt.=294) in 20 ml DMF, were first added 11 mmoles of DCC (mole wt.=206), 3.5 g of H-Lys(Z)-OtBu hydrochloride salt (mole wt.=336). Then 1.13 ml of triethylamine were added while stirring and cooling in ice water. The pH value of the reaction mixture was adjusted to between 7 and 8 by using triethylamine, and the mixture was stirred at room temperature for 24 hours. After evaporating the mother liquor the residue was taken up in 50 ml of ethyl acetate. The organic solution was successively washed three times with 2N KHSO$_4$ solution, three times with saturated sodium hydrogen carbonate solution, and finally three times with saturated saline solution. After drying the ethyl acetate phase over anhydrous sodium sulfate, and filtering off the drying agent the organic phase was evaporated to obtain the title compound as an oil which is triturated in petroleum ether. $R_f(4):0.85$; $R_f(5): 0.65$.

EXAMPLE 9

Preparation of BOC-Glu(OBzl)-Lys(Z)-OtBu

To a solution containing 2.12 g of BOC-Glu(OBzl)-OFFP amino acid active ester (mole wt.=503) in 20 ml DMF, first 744 mg H-Lys(Z)-OtBu hydrochloride salt (mole wt.=371), then 0.28 ml triethylamine were added while stirring and cooling by ice-water. The pH value of the reaction mixture is adjusted between 7 and 8 by using triethylamine and the mixture is stirred at room temperature for 24 hours. After evaporating the mother liquor the residue is taken up in 30 ml of ethyl acetate. The organic solution is successively washed three times with 10% citric acid, three times with saturated sodium hydrogen carbonate solution, and finally three times with saturated saline solution. After drying the organic phase over anhydrous sodium sulfate, the drying agent was filtered off and the organic phase was evaporated to give an oil which was then triturated in petroleum ether and crystallized from ethanol with water to obtain the title compound. $R_f(1):0.95$; m.p.=79–81° C.

EXAMPLE 10

Preparation of BOC-Glu(OBzl)-Lys(2)-OMe

To a solution containing 2.1 g of the amino acid active ester BOC-Glu(OBzl)-OPFP (mole wt.=503) in 10 ml DMF, was first added 1.3 g of H-Lys(Z)-OMe hydrochloride salt (mole wt.=329). Then 0.28 ml of triethylamine were added while stirring and cooling with ice water. The pH value of the reaction mixture was adjusted to between 7 and 8 with triethylamine, and the mixture was stirred at room temperature for 24 hours. After evaporating the mother liquor the residue was taken up in 50 ml of ether. The organic solution was successively washed three times with 2N $KHSO_4$ solution, three times with saturated sodium hydrogen carbonate solution, and finally three times with saturated saline solution. After drying the organic phase over anhydrous sodium sulfate, the arying agent was filtered off, and the organic phase was evaporated to give an oil which was triturated in petroleum ether and crystallized from ethanol with water to obtain the title compound. $R_f(1)=0.80$; $R_f(4):0.85$; $R_f(5):0.90$; m.p.=102–105° C.

EXAMPLE 11

Preparation of $N^\alpha,N^\epsilon$-bis[BOC-Lys (BOC)]-Lys-OMe

To a solution containing 5.12 g of the amino acid active ester BOC-Lys(BOC)-OPFP (mole wt.=512) in 50 ml DMF, was first added 1.15 g of Lys-OMe dihydrochloride salt (mole wt.=231). Then 1.38 ml of triethylamine were added while stirring and cooling with ice water. The pH value of the reaction mixture was adjusted to between 7 and 8 with triethylamine, and the mixture was stirred at room temperature for 24 hours. After evaporating the mother liquor the residue was taken up in 50 ml of ether. The organic solution was successively washed three times with 2N $KHSO_4$ solution, three times with saturated sodium hydrogen carbonate solution, and finally three times with saturated saline solution. After drying the organic phase over anhydrous sodium sulfate, the drying agent was filtered off, and the organic phase was evaporated to give the title compound as an oil. $R_f(1):0.90$; $R_f(4):0.90$.

EXAMPLE 12

Preparation of $N^\alpha,N^\epsilon$-bis[Z-Glu(OtBu)]-Lys-OMe $N^\alpha,N^\epsilon$-bis[(Z-Glu(OtBu)]-Lys-OMe was prepared according to the procedure of example 11, except that 2.5 g of the amino acid active ester Z-Glu(OtBu)-OPFP was used as the starting material, and other constituents were used in the amounts of 0.6 g of Lys-OMe dihydrochloride, 25 ml DMF, and 0.1 ml triethylamine. The title compound is a white crystalline material. $R_f(1):0.70$; $R_f(4):0.75$; m.p.=83–84° C.

Methods for Demonstrating the Efficacy of Reversins

Any of the various Reversin compounds of the invention can be screened for their ability to reduce the activity of the MDR1 protein according to the following in vitro and in vivo methods. In addition to the instructions and experiments provided below, each method is supported by one or more publications, each of which is hereby incorporated by reference.

A. In vitro Methods

Two test systems were developed to specifically assess the ability of a Reversin compound to interact with the human MDR1 protein. The first system measures the ATPase activity of MDR1, while the second system measures the level of a fluorescent indicator extruded by the MDR1 protein.

1. ATPase Assay

In the first assay, MDR1-ATPase activation reflects the interaction and relative affinity MDR1 has for a candidate compound. The MDR1-ATPase is stimulated by cytotoxic drugs, e.g., vincristine, while it is insensitive to chemicals that are not transported by the MDR1 protein. The MDR1-ATPase is also stimulated by known chemosensitizing agents, such as the multidrug-resistance reversing agents verapamil and quinine (FIG. 3), probably competing with drug extrusion of the multidrug transporter. Thus, by measuring this MDR1-ATPase a relatively simple in vitro assay system became available for assessing direct drug interactions with the MDR1 protein (Sarkadi et al. *J. Biol. Chem.* 267:4854–4858, 1992).

The assay was developed by expressing the human MDR1 protein in *Spodoptera frugiperda* insect cells. The cultured cells were infected with a baculovirus into which the cDNA of human MDR1 was genetically engineered. The recombinant virus-infected cells produce a large amount of the MDR1 protein, properly folded and functionally inserted into the membrane. Additional details regarding construction of these recombinant strains are provided by Germann et al. (*Biochemistry* 29:2295–2303, 1988) and Sarkadi et al. (1992 supra).

Measurements of the effect of Reversins on the MDR1 ATPase activity are performed as follows, and according to the methods provided by Sarkadi et al. (1992, supra).

Figure 3:
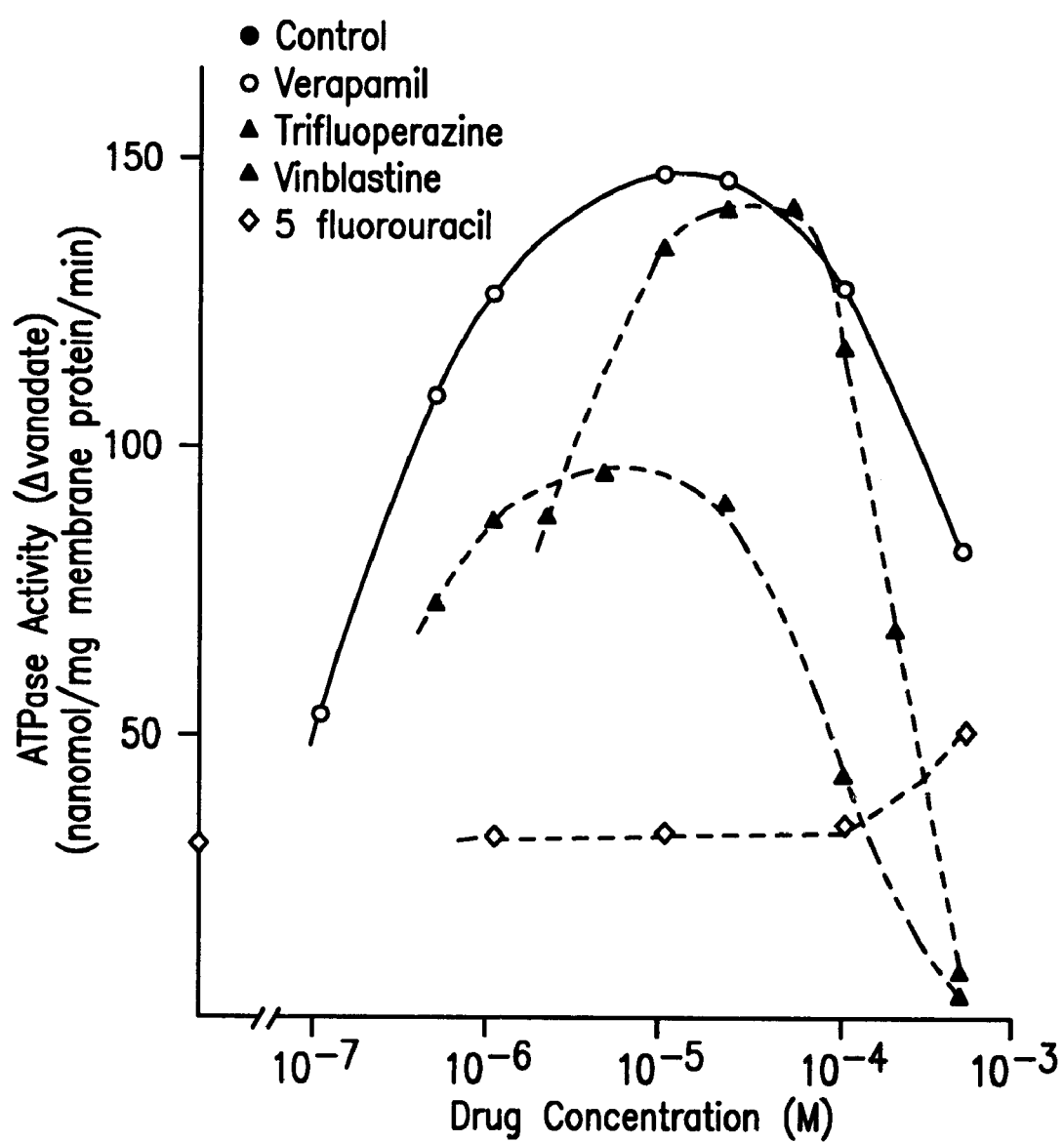
FIG. 3 is a graph showing drug-stimulation of human MDR1-ATPase activity in isolated insect cell membranes.

MDR1 ATPase measurements:

*Spodoptera frugiporda* (Sf9) cells were infected with a recombinant baculovirus carrying the human MDR1 gene, and cultured according to the procedures described previously (Germann et al. 1990 supra; Sarkadi et al. 1992 supra). The virus-infected Sf9 cells were harvested, and their membranes isolated and stored as described (Sarkadi et al. *J. Biol. Chem.* 267:4854–4858, 1992). The amount of ATP consumption measured in these membranes reflects the ATP-dependent transport function of the multidrug transporter. ATPase activity of the isolated Sf9 cell membranes was estimated by measuring inorganic phosphate ($P_i$) liberation. To do this, a membrane suspension (about 10 µg of membrane protein) was incubated at 37° C. in 0.1 ml of a medium containing 50 mM Tris-Mes (pH 6.8), 2 mM EGTA, 2 mM DTT, 50 mM KCl, and 5 mM Na-azide. The ATPase reaction was started by the addition of 5 mM MgATP. The reaction was stopped by the addition of 0.1 ml of 5% SDS solution, and the amount of $P_i$ determined immediately. ATPase activity was estimated by the difference obtained in $P_i$ levels by a sensitive calorimetric assay between zero minutes (reaction stopped immediately with SDS) and 20 minute incubation periods. The data points show the means of triplicate determinations in a representative experiment. The differences between the ATPase activities measured in the absence and presence of vanadate (100 μM) are plotted. Isolated membranes of uninfected or B galactosidase infected Sf9 cells had no drug-stimulated ATPase activity (FIG. 3).

Figure 4:
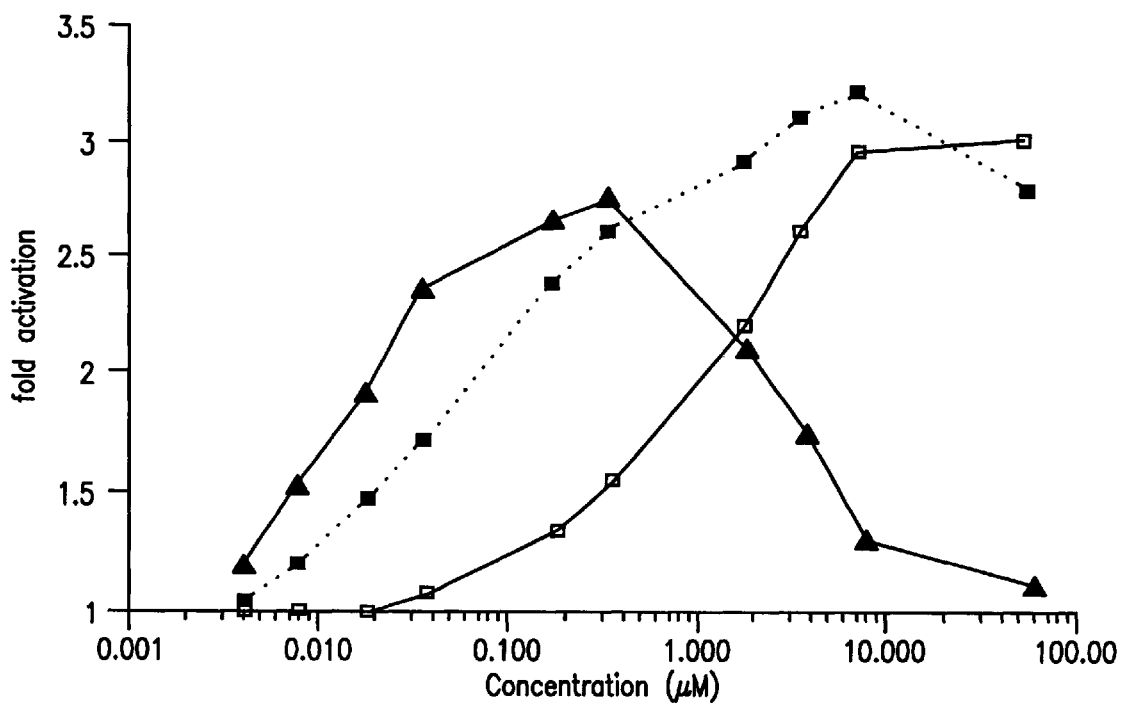
FIG. 4 is a graph showing stimulation of the vanadate-sensitive human MDR1-ATPase activity in the isolated membranes of Sf9 cells by verapamil and Reversins.

When Reversins 121 and 205 were tested in the ATPase assay system, they greatly stimulated the MDR1-ATPase, but were effective at significantly (one to two orders of magnitude) smaller concentrations than the known reversing agents verapamil and quinine. The half-maximal activating concentration ($K_a$) of verapamil was approximately 1 μM, while the $K_a$ value for Reversin 121 was approximately 60 nM and for Reversin 205 this value 20 was about 30 nM (FIG. 4). Thus, the multidrug transporter seems to interact with Reversins with an exceptionally high affinity. As shown in FIG. 4, a strong inhibition of the MDR1-ATPase was observed at higher concentrations (above 1 μM) of Reversin 205.

2. Fluorescence Assay:

The second assay is based on the measurement of fluorescent dye uptake into intact cells. Fluorescent dyes are often used to indicate intracellular calcium or pH changes. An effective technique for cellular dye loading is the application of acetoxy-methylester (AM) derivatives. These hydrophobic dye esters are non-fluorescent outside the cell are cleaved by intracellular esterases into hydrophilic fluorescent free acids. This intracellular "trapping" of the free dye and the continuous inward gradient of the AM compounds results in the accumulation of large amounts of fluorescent indicator inside the cell.

Cell culturing:

NIH 3T3 cells were cultured under standard conditions in D-MEM medium. MDR1-transfected cells (NIH MDR1 G185) were prepared and characterized for their drug-resistant properties as described (Ambdukar et al. *Proc. Natl. Acad. Sci. USA* 89:8472–8476, 1992; Bruggemann et al. *J. Biol. Chem.* 267:21020–21026, 1992; Sarkadi et al. 1992 supra). Before each experiment the cells were trypsinized, then washed and stored in D-MEM medium at 37° C. KBV1 (MDR1$^+$) and KB3 (MDR1$^-$) human tumor cells were also cultured in D-MEM, which K562 human tumor cells were grown in RPMI medium, supplemented with 10% FCS.

Figure 5:
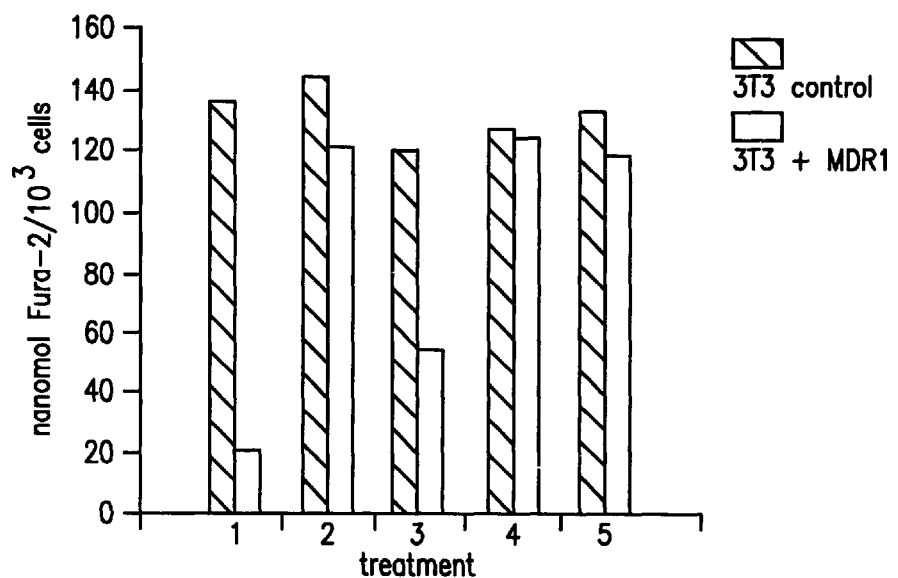
FIG. 5 is a bar graph showing the effects of Reversins on Fura-2 uptake in NIH 3T3 fibroblasts.

The effects of Reversins 121 and 205 on MDR1 function in intact cells was examined by a fluorescent dye extrusion assay (FIG. 5). Mouse NIH 3T3 fibroblasts, transfected with human MDR1 cDNA and expressing human MDR1 protein, actively extrude the hydrophobic AM derivatives of fluorescent dyes, e.g., Fura2-AM (Homolya et al. *J. Biol. Chem.* 29:21493–21496, 1993; Hollo et al. *Bioch. Biophy. Acta.* 1191:384–388, 1994). Similar experiments can be performed with MDR1-expressing human tumor cells. Verapamil, vincristine, and Reversins 121 and 205 inhibit this dye extrusion, most probably by competing with the dye on the transporter. In the experiments shown here maximally effective concentrations of Reversins were used. However, Reversins also act in at least one order of magnitude smaller concentrations than verapamil.

Figure 6:
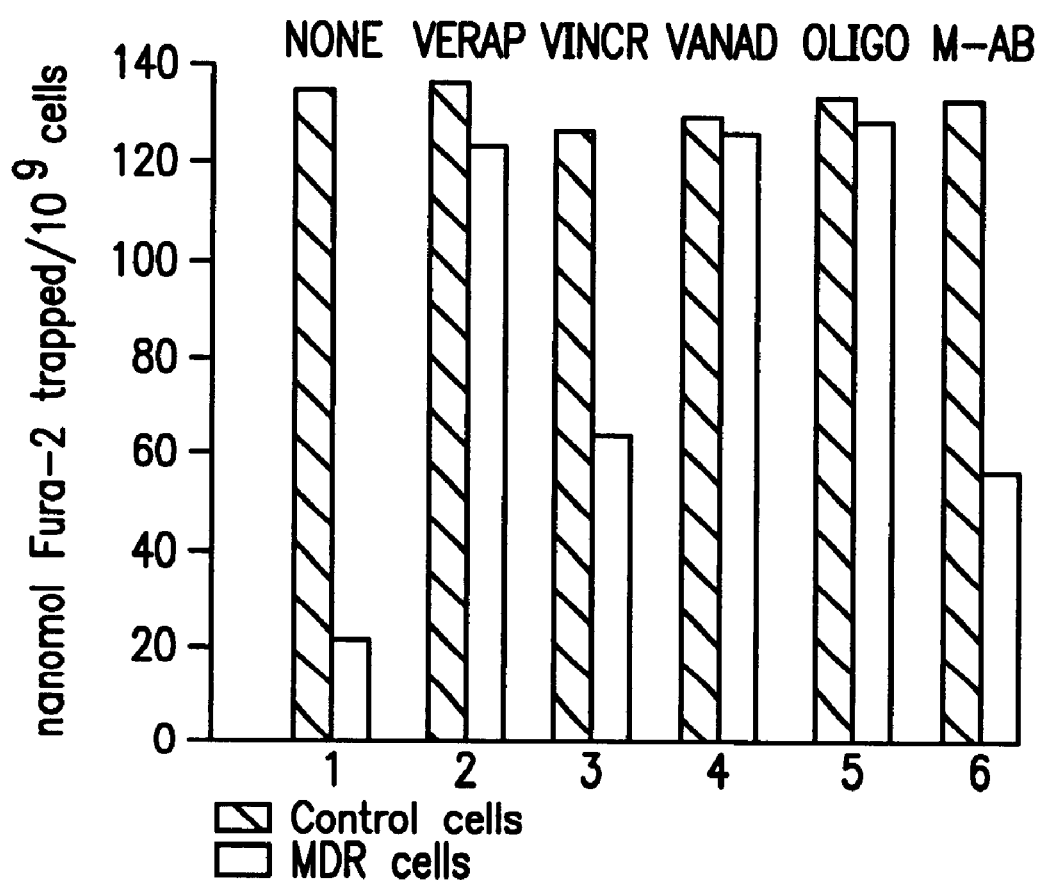
FIG. 6 is a bar graph showing the inhibition of Fura-2 AM loading in MDR1-expressing fibroblasts by agents interacting with MDR1.

Human MDR1-transfected mouse fibroblasts and MDR1-expressing human tumor cells actively extrude the AM forms of several fluorescent indicators, lowering the level of intracellular fluorescence in cells with active multidrug transport. Thus the accumulation in such cells of fluorescent dye is strongly inhibited. This MDR1-specific dye-AM extrusion is blocked by competing substrates and inhibitors of the MDR1 transporter, e.g., by verapamil, vincristine, sodium orthovanadate, and a monoclonal anti-MDR1 antibody. In contrast, these agents have no effect on dye accumulation in fibroblasts which do not overexpress MDR1 (FIG. 6). See also Kessel et al. (*Cancer Res.* 51:665–670, 1991); Neyfakh et al. (*Exp. Cell. Res.* 174:168–176, 1988); and Sarkadi et al. (*J. Biol. Chem.* 268:21493–21496, 1993).

Fluorescence studies:

Dye uptake was measured by incubating $2 \times 10^6$ cells/ml D-MEM medium at 37° C. in the presence of 0.5 μM Fura-2 AM (added in 5 mM stock solution in DMSO), then rapidly spinning the cells (15 sec, 12,000×g), and rinsing the pellet with HPM1 medium (containing 120 mM NaCl, 5 mM kcl, 0.4 mM $MgCl_2$, 0.04 mM $CaCl_2$, 10 mM HEPES-Na (pH 7.4), 10 mM $NaHCO_3$, 10 mM glucose, and 5 mM $Na_2HPO_4$). The cells were resuspended in 2 ml HPM1 and fluorescence was measured with rapid stirring in a Hitachi F-4000 fluorescent spectrophotometer. The excitation wavelength was 340 nm, and emission was measured at 410 nm. Maximum fluorescence and dye concentration were measured after the addition of 0.5% Triton X-100 and 2 mM $CaCl_2$ to the medium. The dye concentration was calibrated based on the measurements of free acid dye fluorescence in the same instrument under identical conditions.

Flow-cytometric measurements:

Fluorescence measurements were done in 60 sec scanning periods using a Cytoronabsolut instrument (Ortho Diagnostic Systems, NJ). The excitation was set to 488 nm. Green fluorescence was measured with a filter with a range of 515–548 nm, while red fluorescence was measured above 620 nm.

With this method drug-interactions with the MDR1 protein can be measured by following cellular fluorescence allowing a flow cytometric or single cell imaging detection of the function of MDR1 in tumor cells. As shown in the single cell images of FIG. 7, fibroblasts expressing the MDR1 protein, in contrast to the control cells, are not loaded with a fluorescent dye, while verapamil, which inhibits the multidrug transporter, restores dye uptake.

When assaying the effect of Reversin molecules on the fluorescent dye uptake and the drug-resistance in various MDR1-transfected and multidrug-resistant tumor cell lines in vitro, these experiments indicated a strong inhibitory action on drug extrusion by low concentrations of Reversins, again showing a specific interaction of the multidrug transporter with these molecules.

Binding Experiments:

The relative ability of Reversins to bind to the MDR1 protein, or to be removed from the cell membrane, is measured by "wash-out experiments" (FIG. 9). NIH 3T3-MDR1 cells were pre-treated with 15 μM verapamil, 5 μM Reversin 121, or 5 μM Reversin 205 for 5 minutes, which produced a complete inhibition of dye extrusion by MDR1 with 1% serum in the media. The cells were washed once with the standard incubation media and a 5 min centrifugation at 800×g. Dye uptake was then measured with or without the addition of 15 μM verapamil during the uptake period. As shown, preincubation with verapamil had no effect on dye uptake, while both Reversin 121 and Reversin 205 had a major effect even after washing the cells. Thus verapamil could be eliminated by a single wash, while 121 and 205 remained effectively bound to MDR1.

Assessing Reversin Activity by its Ability to Enhance the Cytotoxicity Caused by Other Agents Another method for assessing the ability of Reversins to inhibit drug resistance is to measure the cytotoxicity of drugs in multidrug-resistant human tumor cell lines. Since MDR1 normally lowers the concentration of cytotoxic agents to subtoxic concentrations by extruding them from the cell, inhibition of MDR1 would be expected to enhance cytotoxicity.

In these studies, adriamycin, vincristine, and vinblastine, in originally ineffective concentrations, become effectively cytotoxic in the presence of 1–10 μg/ml of Reversins 121 or 205. FIGS. 10A and 10B present such an experiment for Reversin 205 using K562 human erythroblastoid tumor cells and their adriamycin-selected multidrug-resistant subline. FIGS. 11A and 11B are similar experiments with the intestinal tumor cells KB3 and KBV1, the latter being a multidrug resistant subline. In the experiment shown in FIG. 11(A), Reversin 121 was found to be cytotoxic in the MDR1-expressing cells (but not in the control cells) even without the addition vinblastine. Such a collateral toxic effect (which may be due to the ATP-consuming futile functioning of the drug transporter) can be greatly advantageous in treating drug-resistant tumors.

Application of the in Vitro Fluorescent Assay for Clinical Diagnosis

By using the some fluorescent dye extrusion assay described above the in vitro effects of Reversins on the multidrug-resistant leukocytes of a leukemic patient were studied. Cells were isolated by withdrawing blood from the patient, and isolating white blood cells by centrifugation. Cells can be isolated from other types of tumors by biopsy. A flow cytometer was used to measure fluorescent dye loading of individual cells, which had been previously shown to express MDR1, in the absence or presence of Reversin 205 (FIG. 8). The uptake of fluorescent dye under these conditions models the uptake of cytotoxic drugs into the tumor cells. Fluorescent dye uptake was measured at 37° C. for 10 minutes. In FIG. 8, the MDR1 containing cells in the control experiment had a low fluorescent dye uptake (A), while the addition of 5 μM Reversin 205 blocked dye extrusion by MDR1 (B). Reversin 205 thereby significantly increased dye uptake and yielded a uniformly high fluorescence in the leukocytes. Further details for the method are provided by Hollo et al., supra.

Addition in vitro methods:

Additional in vitro methods of screening the ability of a Reversin compound to act as a chemosensitizing agent for the reversal of multidrug resistance are provided by Ford et al. supra, at Tables 1–6.

B. In vivo Methods

In vivo animal studies for the effectiveness of Reversins can be conducted using any suitable animal model system known to those skilled in the art. One example of an appropriate system is the mouse P388 leukemia model system (Tsurouo et al., supra). This animal model is widely accepted for testing the effect of cytotoxic antileukemic agents or response-modifier compounds.

Inbred (DBA×black F1) mice received $10^6$ P388 leukemia cells by intraperitoneal injection. The survival of the mice was followed. The mice were injected with control P388 cells, as well as with P388 cells that had been selected under drug exposure. Drug exposure induced over-expression of the MDR1 protein (P388-MDR cells).

In one trial, the mice had a mean survival time of 14–16 days (they die in a generalized leukemia caused by the P388 cells). The mice injected with the P388 cells were treated with doxorobicin (adriamycin) in a dose of 1 mg/kg/day for 6 days after the injection of the P388 cells. The results showed that adriamycin prolonged the survival time in the case of mice injected with control P388 cells, exceeding the period of 30 days. In contrast, adriamycin therapy did not significantly prolong the lifetime of mice injected with P388-MDR cells. Reversin can be administered to the animals in a dose of 2 mg/kg, a level which has no toxic effect on the control animals, as discussed above.

Another test system is to conduct similar trials using human xenografts in nude mice. Human erythroleukemia (K562) cells are injected into tolerant mice. The developing leukemia is treated with cytotoxic compounds with or without a Reversin candidate compound.

Another animal model system for testing the ability of a Reversin compound to reverse multidrug resistance is to use a transgenic mouse which expresses the human MDR1 gene, e.g., in its bone marrow (Pastan et al. FASEB Jour. 5:2523–2528, 1991).

Human clinical trials can be performed according to methods known to those skilled in the art. For example, Dalton et al. provide methods of testing the chemosensitizer verapamil for its ability to modify resistance to a chemotherapeutic (Jour. Clin. Oncol. 7:415–424, 1989). Additional methods for conducting human clinical trials of Reversins include, but are not limited to, those provided by Berenbaum et al. (Pharmacol. Rev. 41:93–141, 1989); Benson et al. (Cancer Treat. Rep. 69:795–799, 1985); Cairo et al. (Cancer Res. 49:1063–1066, 1989); Fine et al. (J. Clin. Oncol. 5:489–10 495, 1987); Frishman et al. (J. Cardiol. 50:1180–1184, 1982); Miller et al. (J. Clin. Oncol. 6:880–888, 1988); Ozols et al. (J. Clin. Oncol. 5:641–647, 1987); and Presant et al. (Am. J. Clin. Oncol. 9:355–357, 1986).

Therapeutic Use of Reversins

The Reversins of the invention can be used therapeutically to inhibit the in vivo activity of the MDR1 protein in a patient experiencing drug resistance or poor drug absorption. An effective amount of the Reversin can be administered intravenously to the patient, or administered orally according to conventional methods, in the form of a capsule, liquid, tablet, powder, or pill. Reversin can also be incorporated into an implanted or orally administered slow release device.

Reversin can be prepared for therapeutic use by mixing the compound with pharmaceutical carriers and/or additives that aid solubility, absorption, flavor, or texture to the vehicle or its contents, e.g., physiological saline, oil, e.g., refined soy bean oil, gelatin, glycerin, or purified water.

An appropriate dosage is between 50 μg/kg and 100 mg/kg. An effective and safe dosage can be determined by conventional methods or by the methods taught herein, or by calibration to a given patient on an individual basis.

It has been found that compounds of the formula (I) according to our invention are capable of stimulating, in a concentration of 0.03 μM, or of inhibiting, respectively, in concentrations of 1 to 5 μM, the activity of the MDR1 protein. The stimulating concentrations are by 1 to 3 orders, the inhibitory concentrations are by 1 to 2 orders lower than the corresponding concentrations of substances known from the literature, e.g., verapamil.

The safety of Reversins for human administration can be confirmed in appropriate animal models. For example, the in vivo acute and subacute toxicity of Reversins was examined in laboratory rats. Reversins 121 and 205 solutions were prepared and administered as follows. Type A solutions contained 50 μg/ml Reversin 121 or 205 in 20% ethanol in physiological saline. Type B solutions contained 1 mg/ml in glycerol, containing 10% ethanol. Type A solutions (0.5 ml) were administered intravenously to three laboratory rats weighing 200–250 g each (about 100–125 μg/kg) twice daily for 3 days. Type B solutions (0.5 ml) were given to similar rats (2–2.5 mg/kg) by intraperitoneal injection, twice daily for three days. Control rats received the same solutions without the Reversins. During the three days of injections and in a two-week follow-up period, no acute or subacute toxicity of the compounds was observed.

Additional toxicity testing can be performed by the methods of Pastan et al. (*Proc. Natl. Acad. Sci. USA* 85:4486–4490, 1988) and Tsuruo et al. (*Cancer Res.* 43:2905–2910, 1983).

Other embodiments are within the claims set forth below.

What is claimed is:

1. A method for reducing the activity of the multidrug transporter protein in a mammal, said method comprising administering to said mammal an effective amount of a compound BOC-Asp(OBzl)-Lys(Z)-OtBu, or $N^\alpha,N^\epsilon$-bis[BOC-Glu(OBzl)]-Lys-OMe.

2. The method of claim 1, wherein said method is used to lower resistance to a drug.

3. The method of claim 2, wherein said drug is selected from the group consisting of a chemotherapeutic drug, an antiparasitic drug and an antibiotic drug.

4. The method of claim 1, wherein said method is used to facilitate administration of a drug through the blood-brain barrier or through the blood-testis barrier.

5. The method of claim 1, wherein said compound of the formula (I) is co-administered with a drug.

6. The method of claim 5, wherein said drug is selected from the group consisting of a chemotherapeutic drug, an antiparasitic drug and an antibiotic drug.

7. A peptide compound selected from the group consisting of BOC-Asp(OBzl)-Lys(Z)-OtBu, succinyl-bis[Glu(OBzl)-OBzl], Z-D-Glu-(OBzl)-D-Asp(OBzl)-OBzl, DBTA-bis(D-Phe-Trp-OMe), DBTA-[Glu(O-Bzl)$_2$], $N^\alpha,N^\epsilon$-bis[BOC-Glu(OBzl)]-Lys-OMe, BOC-Tyr(Bzl)-Tyr-(Bzl)-OMe, BOC-D-Ser(Bzl)-Lys(Z)-OtBu, BOC-Glu(OBzl)-Lys(z)-OtBu, $N^\alpha,N^\epsilon$-bis[BOC-Lys(BOC)]Lys-OMe and $N^\alpha,N^\epsilon$-bis[Z-Glu(OtBu)]Lys-OMe.

8. A composition comprising the compound defined in claim 7 which is BOC-Asp(OBzl)-Lys(Z)-OtBu or $N^\alpha,N^\epsilon$-bis[BOC-Glu-(OBzl)]-Lys-OMe and a pharmaceutically acceptable carrier.

9. A composition comprising the compound defined in claim 7 which is BOC-Asp(OBzl)-Lys(Z)-OtBu or $N^\alpha,N^\epsilon$-bis[BOC-Glu-(OBzl)]-Lys-OMe and a drug.

* * * * *

UNITED STATES PATENT AND TRADEMARK OFFICE
CERTIFICATE OF CORRECTION

PATENT NO.   : 6,297,216 B1
DATED        : October 2, 2001
INVENTOR(S)  : Sarkadi et al.

It is certified that error appears in the above-identified patent and that said Letters Patent is hereby corrected as shown below:

<u>Title page,</u>
Item [57], ABSTRACT,
Line 9, "alkyla-nine" should be -- alkylamine --;
Line 23, "phenylethylarnide" should be -- phenylethylamide --.

Signed and Sealed this

Twenty-sixth Day of February, 2002

Attest:

JAMES E. ROGAN
*Attesting Officer*   *Director of the United States Patent and Trademark Office*